US008914101B2

(12) United States Patent
Hettrick et al.

(10) Patent No.: US 8,914,101 B2
(45) Date of Patent: Dec. 16, 2014

(54) SYSTEM AND METHOD TO LOCALIZE CHANGES IN INTRATHORACIC FLUID CONTENT USING MEASURED IMPEDANCE IN AN IMPLANTABLE DEVICE

(75) Inventors: Douglas A. Hettrick, Andover, MN (US); Shantanu Sarkar, Roseville, MN (US); Todd M. Zielinksi, Ham Lake, MN (US); Kevin P. Knox, Solon, OH (US)

(73) Assignee: Medtronic, Inc., Minneapolis, MN (US)

( * ) Notice: Subject to any disclaimer, the term of this patent is extended or adjusted under 35 U.S.C. 154(b) by 973 days.

(21) Appl. No.: 12/261,131

(22) Filed: Oct. 30, 2008

(65) Prior Publication Data

US 2010/0113962 A1    May 6, 2010

(51) Int. Cl.
*A61B 5/053* (2006.01)
*A61B 5/00* (2006.01)

(52) U.S. Cl.
CPC .......... *A61B 5/0536* (2013.01); *A61B 5/0538* (2013.01); *A61B 5/0537* (2013.01); *A61B 5/4878* (2013.01)
USPC .......................................... 600/547; 600/382

(58) Field of Classification Search
CPC .. A61B 5/0536; A61B 5/4878; A61B 5/0538; A61B 5/0537
USPC ................................................ 600/547, 382
See application file for complete search history.

(56) References Cited

U.S. PATENT DOCUMENTS

| | | | |
|---|---|---|---|
| 5,919,142 A | | 7/1999 | Boone et al. |
| 6,055,448 A | | 4/2000 | Anderson et al. |
| 6,411,095 B1 | * | 6/2002 | Chin et al. .................. 324/326 |
| 6,501,984 B1 | * | 12/2002 | Church et al. ............... 600/547 |
| 6,512,949 B1 | * | 1/2003 | Combs et al. ................ 600/547 |
| 6,845,264 B1 | * | 1/2005 | Skladnev et al. ............ 600/547 |
| 7,096,061 B2 | | 8/2006 | Arad |
| 7,226,422 B2 | * | 6/2007 | Hatlestsad et al. ........... 600/534 |
| 7,371,220 B1 | * | 5/2008 | Koh et al. .................... 600/529 |
| 7,387,610 B2 | * | 6/2008 | Stahmann et al. ........... 600/538 |
| 7,496,450 B2 | * | 2/2009 | Ortiz Aleman et al. ......... 702/6 |
| 7,672,718 B2 | * | 3/2010 | Stahmann et al. ........... 600/547 |
| 7,778,708 B1 | * | 8/2010 | Koh et al. ..................... 607/17 |
| 7,925,349 B1 | * | 4/2011 | Wong et al. ................... 607/28 |

(Continued)

FOREIGN PATENT DOCUMENTS

| | | |
|---|---|---|
| GB | 2138148 A | 10/1984 |
| WO | WO 2006042039 A2 * | 4/2006 |
| WO | WO 2008014078 A2 * | 1/2008 ............. G06F 19/00 |
| WO | 2008105692 A1 | 9/2008 |

OTHER PUBLICATIONS

Adler et al. "Imagine of Pulmonary Edema with Electrical Impedance Tomography" Engineering in Medicine and Biology Society, 1995., IEEE 17th Annual Conference (vol. 1) Sep. 20-25, 1995.*

(Continued)

*Primary Examiner* — Jeffrey G Hoekstra
*Assistant Examiner* — Michael C Stout
(74) *Attorney, Agent, or Firm* — Michael C. Soldner (57) ABSTRACT

An implantable medical device and associated methods monitor thoracic fluid status and discriminate thoracic fluid conditions. Intrathoracic impedance is measured along multiple intrathoracic measurement vectors using implanted electrodes. A map of thoracic conductivity is computed using the measured intrathoracic impedances. A thoracic fluid condition is detected in response to the computed map.

20 Claims, 6 Drawing Sheets

(56) References Cited

U.S. PATENT DOCUMENTS

| | | | |
|---|---|---|---|
| 8,065,005 B1* | 11/2011 | Wong et al. .................. 607/28 | |
| 2004/0133123 A1 | 7/2004 | Leonhardt et al. | |
| 2005/0080460 A1* | 4/2005 | Wang et al. .................. 607/17 | |
| 2005/0090753 A1 | 4/2005 | Goor et al. | |
| 2005/0107719 A1* | 5/2005 | Arad (Abbound) .......... 600/547 | |
| 2005/0107833 A1* | 5/2005 | Freeman et al. .................. 607/5 | |
| 2005/0107834 A1 | 5/2005 | Freeman et al. | |
| 2006/0004301 A1 | 1/2006 | Kasevich | |
| 2006/0064029 A1 | 3/2006 | Arad | |
| 2006/0184060 A1* | 8/2006 | Belalcazar et al. ........... 600/547 | |
| 2006/0235325 A1 | 10/2006 | Holmstrom et al. | |
| 2006/0264776 A1* | 11/2006 | Stahmann et al. ........... 600/547 | |
| 2007/0118042 A1* | 5/2007 | Wang ........................... 600/508 | |
| 2007/0135725 A1* | 6/2007 | Hatlestad ..................... 600/529 | |
| 2007/0270707 A1* | 11/2007 | Belalcazar ................... 600/547 | |
| 2007/0282185 A1* | 12/2007 | Belalcazar ................... 600/345 | |
| 2008/0027349 A1* | 1/2008 | Stylos ........................... 600/547 | |
| 2008/0058656 A1* | 3/2008 | Costello et al. .............. 600/508 | |
| 2008/0108907 A1* | 5/2008 | Stahmann et al. ........... 600/529 | |
| 2008/0125826 A1* | 5/2008 | Belalcazar et al. ............. 607/17 | |
| 2008/0183072 A1* | 7/2008 | Robertson et al. ........... 600/425 | |
| 2008/0249433 A1* | 10/2008 | Stahmann et al. ........... 600/547 | |
| 2008/0262379 A1* | 10/2008 | Gerber et al. ................. 600/549 | |
| 2009/0143663 A1* | 6/2009 | Chetham ....................... 600/372 | |
| 2010/0152605 A1* | 6/2010 | Ward ............................ 600/547 | |

OTHER PUBLICATIONS

Wolf GK, et al. "Noninvasive assessment of lung volume: Respiratory inductance plethysmography and electrical impedance tomography." Crit Care Med 2005, S163-S169, 33(3) Supplement.

Coulombe N et al. "A parametric model of the relationship between EIT and total lung volume" Physiol Meas 2005 pp. 401-411. vol. 26(4).

Zhang J et al. "EIT images of ventilation: What contributes to the resistivity changes?" Physiolo Meas 2005 pp. S81-S92 vol. 26(2).

Yu CM, et al. "Intrathoracic impedance monitoring in patients with heart failure: Correlation with fluid status and feasibility of early warning preceding hopitalization" Circulation. 2005 pp. 841-848. vol. 112 (6).

Vollman D et al. "Clinical utility of intrathoracic impedance monitoring to alert patients with an implanted device of deteriorating chronic heart failure." Eur Heart J Aug. 2007 pp. 1835-1840. vol. 28(15).

Bayford RH, "Bioimpedance tomography", Annu Rev Biomed Eng. 2006 pp. 63-91. vol. 8.

(PCT/US2009/059152) International Search Report.

* cited by examiner

SYSTEM AND METHOD TO LOCALIZE CHANGES IN INTRATHORACIC FLUID CONTENT USING MEASURED IMPEDANCE IN AN IMPLANTABLE DEVICE

TECHNICAL FIELD

The invention relates generally to implantable medical devices and, in particular, to device and associated methods for monitoring changes in intrathoracic impedance.

BACKGROUND

Intrathoracic impedance measurements can be performed by an implantable medical device (IMD), such as a pacemaker or implantable cardioverter defibrillator (ICD). Intrathoracic impedance measurements are typically made by measuring the impedance between two implanted cardiac electrodes or between a cardiac electrode and the IMD housing. The intrathoracic impedance measurement provides impedance across a portion of the thorax, which may include any portion of the heart, lungs and/or pulmonary vascular bed. Intrathoracic impedance decreases when thoracic fluid level increases, for example with pulmonary edema associated with worsening congestive heart failure. The impedance decreases because of the relatively low resistivity of biological fluids. As such, monitoring intrathoracic impedance is useful in monitoring the status of a heart failure condition.

Other changes that may cause an increase or decrease in intrathoracic impedance include ventricular dilation, vascular dilation, dehydration, hemorrhage, tamponade, pleural effusion, infection, electrolyte imbalance (e.g., hypercalcemia), and anemia. As such, a single intrathoracic impedance measurement can be useful in detecting a change in thoracic fluid status but may not be specific as to the location or underlying cause.

DETAILED DESCRIPTION

In the following description, references are made to illustrative embodiments. It is understood that other embodiments may be utilized without departing from the scope of the invention. For purposes of clarity, the same reference numbers are used in the drawings to identify similar elements. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

Figure 1:
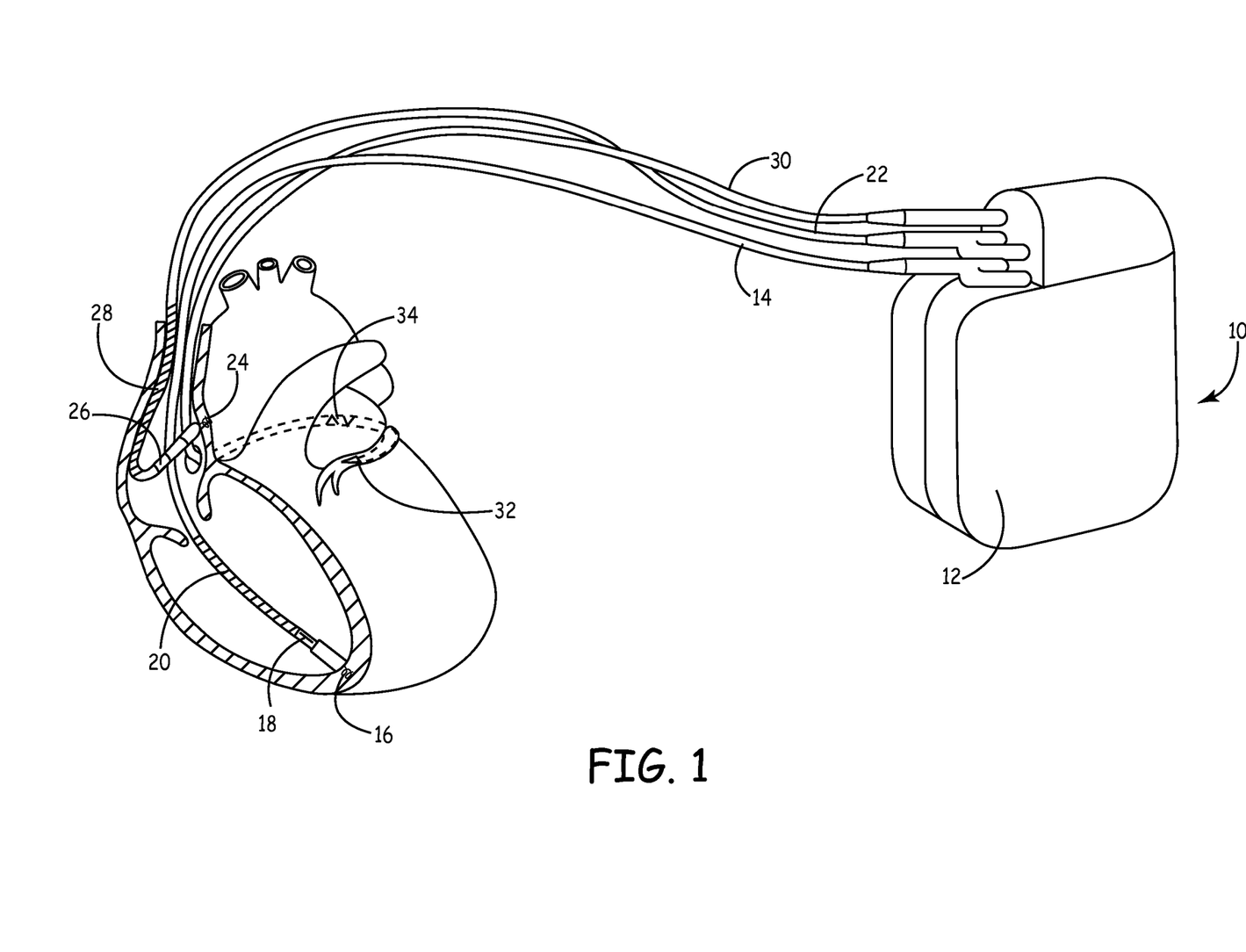
FIG. 1 is a schematic diagram of an implantable medical device system for discriminating thoracic fluid conditions.

FIG. 1 is a schematic diagram of an implantable medical device system for discriminating thoracic conditions using impedance measurements. Discrimination of thoracic conditions is based on changes in tissue conductivity of thoracic anatomical regions detected using a fully implanted electrode system for accumulating intrathoracic impedance measurements Using computational techniques, for example adapted from electrical impedance tomography (EIT) computational methods, a conductivity map is generated based on electrical impedance measurements obtained by an IMD 10 using available fully implanted electrodes.

Examples described herein primarily relate to detecting and discriminating thoracic fluid conditions such as pulmonary edema, cardiac dilation, acute anemia, implanted device pocket infection, etc. In the illustrative system shown, IMD 10 includes a conductive, hermetically-sealed housing 12 enclosing IMD components (not shown). Housing 12 can be used as an electrode in combination with any of the other electrodes shown for performing intrathoracic impedance measurements. Alternatively, electrodes may be incorporated along IMD housing 12.

A right ventricular (RV) lead 14 is shown extending from IMD 10 carrying an RV tip electrode 16, RV ring electrode 18, and RV coil electrode 20. A right atrial (RA) lead 22 extends from IMD 10 into the right atrium for deploying a RA tip electrode 24, RA ring electrode 26, and superior vena cava (SVC) coil electrode 28. A third, coronary sinus (CS) lead 30 is shown advanced into the coronary sinus ostium for positioning a left ventricular (LV) tip electrode 32 and an LV ring electrode 34 along the coronary sinus or a cardiac vein.

IMD 10 is embodied as an implantable cardioverter defibrillator capable of pacing and sensing in the right ventricle using RV tip electrode 16 and RV ring electrode 18, in the left ventricle using LV tip electrode 32 and LV ring electrode 34, and in the right atrium using RA tip electrode 24 and RA ring electrode 26. IMD 10 senses intracardiac EGM signals for detecting and discriminating cardiac rhythms. In response to detecting arrhythmias, IMD 10 may deliver anti-arrhythmia pacing using any of the pacing electrodes 16, 18, 24, 26, 32 and 34 or cardioversion/defibrillation shocks using RV and SVC coil electrodes 20 and 28 and housing 12.

As will be described herein, the electrodes coupled to IMD 10, including housing 12, are sequentially selected in pairs to deliver an excitation signal. For each selected excitation signal pair, the remaining electrodes are sequentially selected in impedance measuring pairs to acquire electrical impedance data for computing a conductivity map.

Figure 2:
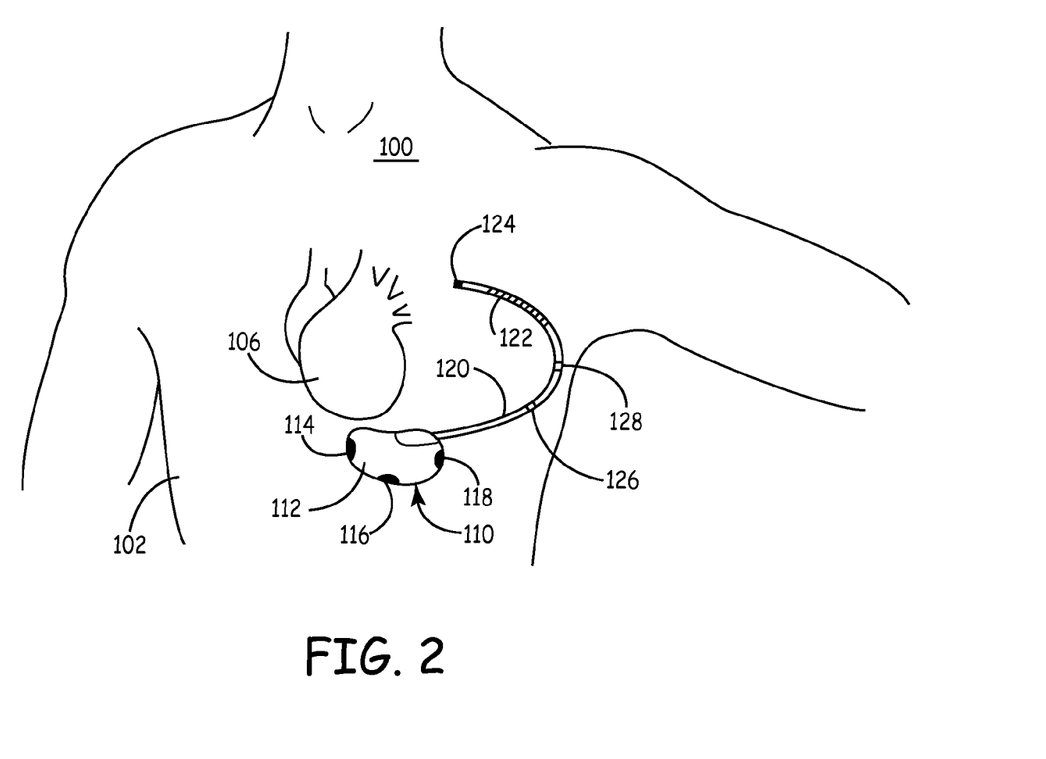
FIG. 2 is a schematic diagram of an alternative IMD system in which thoracic fluid condition discrimination may be implemented.

FIG. 2 is a schematic diagram of an alternative IMD system 100 in which discrimination of thoracic fluid conditions and discrimination may be implemented. IMD system 100 is a subcutaneously implanted ICD system including IMD 110 implanted outside the ribcage of patient 102. A subcutaneous sensing and cardioversion/defibrillation therapy delivery lead 120 is electrically coupled to IMD 110 and tunneled subcutaneously laterally and posteriorly toward the patient's spinal cord, e.g., into a location adjacent to a portion of a latissimus dorsi muscle of patient 102. Lead 120 is tunneled subcutaneously from the median implant pocket of IMD 110 to the patient's back to a location opposite the heart such that the heart 106 is disposed between the IMD 110 and the distal electrode coil 122 and distal sensing electrode 124 of lead 120.

IMD 110 includes housing 112 enclosing IMD circuitry (not shown) and supporting subcutaneous sensing electrodes 114, 116, and 118 mounted along housing 112 and electrically coupled to IMD circuitry within housing 112. Subcutaneous sensing electrodes 114, 116 and 118, and lead-based electrodes 122 and 124 may be used in sequentially selected pairs for injecting an excitation signal and for measuring intrathoracic impedances for use in computing a conductivity map. Additional dedicated electrodes 126 and 128 may be positioned at spaced apart locations along lead 120 for providing additional impedance measurement vectors in combination with the electrodes typically available in a subcutaneous ICD system 100. Electrodes used in measuring intrathoracic impedances may therefore be implanted within the thoracic cavity or along the thoracic wall, inside or outside of the rib cage.

Figure 3:
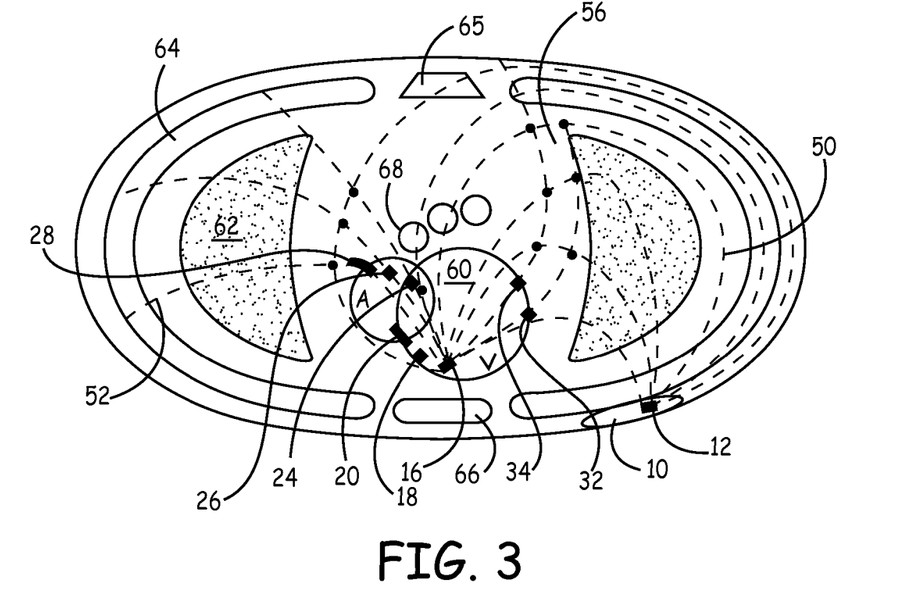
FIG. 3 is a schematic diagram of an intrathoracic electrical impedance measurement method using the IMD system shown in FIG. 1.

FIG. 3 is a schematic illustration of a sectional view of a patient's thorax depicting an intrathoracic impedance measurement method using the IMD system shown in FIG. 1. The heart 60, lungs 62, rib cage 64, spinal cord 65, sternum 66, and great vessels 68 are shown. Tip and ring electrodes 16, 18, 24, 26, 32 and 34 are represented by square symbols and coil electrodes 20 and 28 are represented as rectangular symbols. Any of the RV tip and ring electrodes 16 and 18, RV coil electrode 20, RA tip and ring electrodes 24 and 26, SVC coil electrode 28, LV tip and ring electrodes 32 and 34 and housing 12 are selected two at a time as an excitation electrode pair to inject a current signal. Impedance between each of the remaining electrode pair combinations is measured. Impedance measurements would continue until each desired pair has been selected as the excitation electrode pair and impedance measurements have been recorded for each of the remaining possible electrode pair combinations.

It is to be understood that numerous electrode arrangements could be used for performing intrathoracic impedance measurements for discriminating thoracic fluid conditions. In the arrangement shown in FIGS. 1 and 3, existing pacing, sensing and high-voltage coil electrodes utilized for pacing and cardioversion/defibrillation therapies are used for performing impedance measurements. All or any subset of the available electrodes may be used in to achieve desired excitation and measurement pair combinations. Other electrode and lead arrangements that could be used in an implantable device system may result in more or fewer electrodes being positioned at various locations within or along the thorax than the arrangement shown in FIG. 3. Furthermore, it is recognized that additional dedicated electrodes may be placed for the purpose of providing additional impedance measuring vectors. Such electrodes may be carried by transvenous or subcutaneous leads.

In the example shown in FIG. 3, the IMD housing 12 and the RV tip electrode 16 are selected as the drive electrode pair injecting an excitation current signal and thereby creating isopotential lines 50. Intrathoracic impedances will be determined from the measured voltage between remaining pairs of electrodes, defining multiple impedance measurement vectors 52. In the example shown, measurement vectors 52 are shown extending between the RV tip electrode 16 and the RA electrodes 24, 26 and 28 and the LV electrodes 32 and 34. Additional measurement vectors may be selected but are not shown for the sake of clarity. The electrodes included in the excitation electrode pair may or may not be selected for use in measurement pair combinations.

The measurement vectors 52 and isopotential lines 50 intersect to create a "grid" of mapping "pixels" 56 within the thorax. Pixels 56, also referred to herein as "mapping locations", define the resolution of a conductivity map to be generated based on the internally measured impedances using a system of wholly implanted electrodes. Because of the non-uniform arrangement of the implanted electrodes, pixels 56 will tend to be irregular in shape and size and will likely be distributed unevenly through the thorax. The more electrodes used for measuring impedance, the more measurement vectors there will be and resultant pixels. The number of pixels will determine the resolution of the computed conductivity map.

The resolution will generally be non-uniform in that some areas within the thorax will be mapped with greater resolution and some with relatively less resolution due to the non-uniform spatial arrangement of the electrodes. Furthermore, computed pixel conductivity, although expressed in two dimensions, may be influenced by tissues outside a two-dimensional plane. Even though available electrodes will generally not be positioned within a single plane through the thorax, the resultant conductivity map should provide sufficient accuracy to locate the general region of an acute drop in measured impedance.

Figure 4:
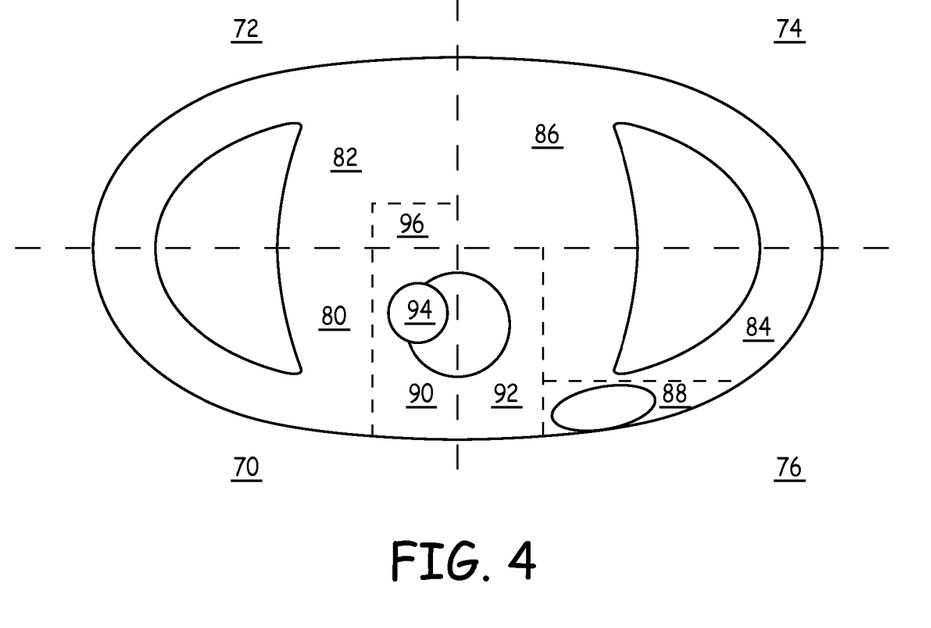
FIG. 4 is a diagram of anatomical regions approximated by impedance measurements.

FIG. 4 is a diagram of anatomical regions approximated by impedance measurements. Each of the pixels 56, alone or in combination with other pixels, will be used to approximate an anatomical region of the thoracic cavity. Anatomical regions approximated by one or more pixels 56, may be identified, for example, as a left lung anterior portion 80, right lung anterior portion 84, left lung posterior portion 82, right lung posterior portion 86, ventricle 90 and 92 (right and left), atrium 94 (which may be further divided between right and left), IMD implant pocket 88, and pulmonary vascular bed 96. The number and specific anatomical regions that can be approximated by the pixels will depend on the electrode arrangement and resulting measurement vectors. In one embodiment, the anatomic regions of the thoracic cavity may be defined as general regions rather than as anatomical structures, e.g., a right posterior portion 76, left posterior portion 70, right anterior portion 74, and left anterior portion 72. In a method for discriminating thoracic fluid conditions, the anatomic regions approximated by pixels exhibiting increased or decreased conductivity are identified. A thoracic fluid condition is then detected based on the change in mapped conductivity and the identified anatomic region(s).

Figure 5:
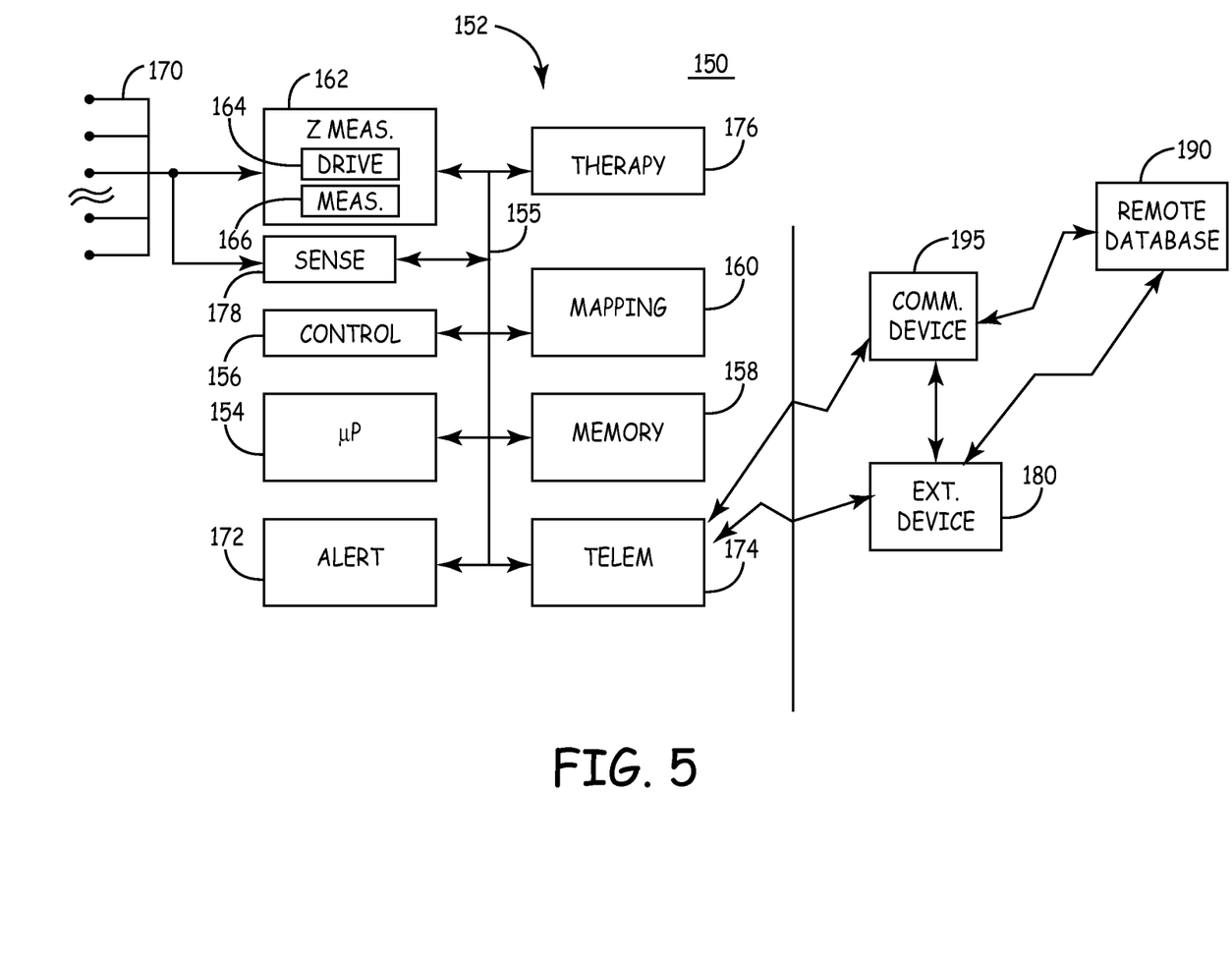
FIG. 5 is a functional block diagram of one embodiment of an IMD system.

FIG. 5 is a functional block diagram of one embodiment of an IMD system. System 150 includes an IMD 152 coupled to a set of implanted electrodes 170, an external device 180 in bidirectional communication with IMD 152, a communication device 195 and a remote database 190.

IMD 152 generally includes control circuitry 156 and an operating system that may employ microprocessor 154 or a digital state machine for timing sensing and therapy delivery functions (when present) in accordance with a programmed operating mode. Microprocessor 154 and associated memory 158 are coupled to the various components of IMD 152 via a data/address bus 155. IMD 152 optionally includes therapy delivery module 176 for delivering a therapy in response to determining a need for therapy based on input from external device 180 or sensed physiological signals. Therapy delivery module 176 may provide drug delivery therapies or electrical stimulation therapies, such as cardiac pacing or arrhythmia therapies.

Electrodes 170 are coupled to an impedance measurement module 162 which includes drive signal circuitry 164 and measurement circuitry 166 for measuring the impedance between various pairs of electrodes 170 in response to an excitation signal. Impedance measurement methods generally include delivering an excitation current signal along an excitation path between a selected pair of electrodes. The voltage is then measured across a pair of measuring electrodes allowing the impedance across the measurement path to be computed from the known excitation signal and the measured voltage. Impedance measurement methods may alternatively involve delivering an excitation voltage signal and measuring a current along the measurement path. As described herein, electrodes 170 are sequentially selected in pairs for delivering a drive signal with impedance measurements performed between remaining electrode pairs in a sequential manner.

Impedance measurements may be scheduled to be performed to reduce any likelihood of interfering with other sensing and therapy delivery functions of the device. For example, during cardiac pacing, impedance measurements may be scheduled to occur during device blanking or refractory periods following ventricular pacing pulses, e.g., with one measurement vector used per cardiac cycle, so that drive signals do not interfere with cardiac sensing. If an arrhythmia is detected requiring an arrhythmia therapy, impedance measurements may be temporarily suspended.

The impedance measuring module 162 provides impedance signals or data to microprocessor 154 for use in computing a conductivity map. Alternatively, impedance data may be transmitted to external device 180 using telemetry module 174. External device 180 may be a programmer or home monitor with a processor for computing the conductivity map and performing thoracic fluid detection and discrimination algorithms. Alternatively, external device 180 may transfer data to a remote database 190 used for remote patient management. The conductivity map computations and/or thoracic fluid condition detection and discrimination may be performed by a remote computer associated with remote database 190.

Communication device 195 may be a cellular phone or other handheld device enabled for wireless communication with IMD 152, external device 180, and/or remote database 190 to receive patient and/or clinician notifications from IMD 152, external device 180 or remote database 190 regarding the patient's thoracic fluid status. Communication devices and networks for use with implantable device systems are generally disclosed, for example, in U.S. Pat. No. 6,418,346 (Nelson, et al.), incorporated herein by reference in its entirety.

Any of electrodes 170 may also be used for receiving cardiac electrical signals. Cardiac electrical signals may be monitored for use in diagnosing or monitoring a patient condition or may be used for determining when a therapy is needed and in controlling the timing and delivery of the therapy. When used for sensing, electrodes 170 are coupled to sensing circuitry 178, which may include sense amplifiers, comparators and an analog-to-digital converter, for sensing cardiac events and providing sense signals to control module 156 and microprocessor 154. Sensed cardiac events may then be used by microprocessor 54 for detecting and discriminating cardiac arrhythmias or other changes in the cardiac EGM signal.

Memory 158 stores a variety of programmed-in operating mode and parameter values that are used by microprocessor 154 in controlling device operations. The memory 158 may also be used for storing data compiled from sensed and measured signals and/or relating to device operating history for telemetry out on receipt of a retrieval or interrogation instruction. A thoracic fluid monitoring algorithm may be stored in memory 158 and executed by microprocessor 154. The thoracic fluid monitoring algorithm includes an impedance measurement algorithm for acquiring intrathoracic impedance measurements and a detection and discrimination algorithm for discriminating thoracic fluid conditions using the measured impedances. Alternatively, mapping module 160 may be provided as dedicated circuitry for receiving intrathoracic impedance measurements from measurement module 162 and for computing a map of thoracic conductivity.

The mapped conductivity data may then be used by microprocessor 154 or transmitted to external device 180 for use in a thoracic fluid condition detection and discrimination algorithm. Microprocessor 154 may respond to a detected thoracic fluid condition by altering a therapy, triggering data storage, enabling other sensors for acquiring physiological data, or triggering alert 172 to generate an alert signal to the patient that a serious condition has been detected that may require medical intervention. Data relating to the detected thoracic fluid condition may be stored in memory 158 for later retrieval. Telemetry module 174 may be used to transmit a notification and data relating to the detected thoracic fluid condition to external device 180 or communication device 195.

Figure 6:
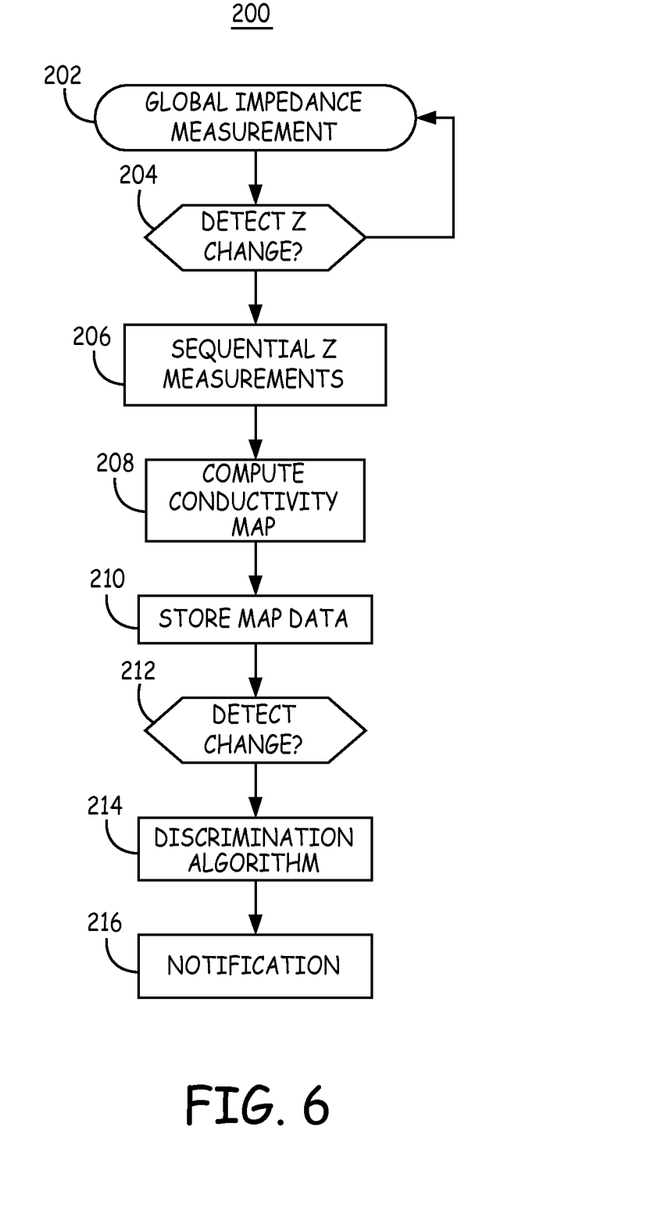
FIG. 6 is a flow chart of a method for detecting and discriminating thoracic fluid conditions.

FIG. 6 is a flow chart of a method 200 for detecting and discriminating thoracic fluid conditions. Flow chart 200 is intended to illustrate the functional operation of the device, and should not be construed as reflective of a specific form of software or hardware necessary to practice the methods described. It is believed that the particular form of software will be determined primarily by the particular system architecture employed in the device and by the particular detection and therapy delivery methodologies employed by the device. Providing software to accomplish the described functionality in the context of any modern IMD, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, hard disk drive, and the like. The instructions may be implemented as one or more software modules, which may be executed by themselves or in combination with other software.

At block 202, an initial intrathoracic impedance measurement is made to assess the thoracic impedance. The impedance measurement made at block 202 is intended to be a relatively global impedance measurement that is sensitive to thoracic impedance changes but with limited or low specificity as to the location of the impedance changes. As such, the measurement pathway used for the initial intrathoracic impedance measurement may be selected to include a greater portion of the thorax than alternative measurement pathways. Alternatively, two or more measurement pathways may be selected for an initial global assessment of the thoracic impedance.

If a change in the global impedance measurement(s) is detected at block 204, sequential impedance measurements are initiated at block 206 for acquiring the data needed to generate a conductivity map for localizing the globally-detected impedance change and discriminating a thoracic fluid condition. The impedance measurement at block 202 may include a single measurement or a series of measurements. For example, detecting a change in global impedance at block 204 may involve computing a mean value, a running average, or a cumulative sum of the differences between measured impedances and a baseline impedance. A cumulative summation method for detecting impedance changes is generally disclosed PCT Publication WO 2008/014078 (Stylos), incorporated herein by reference in its entirety Blocks 202 and 204 allow an initial non-specific detection of a thoracic impedance change to trigger additional impedance measurements and the more computationally intensive methods for discriminating a thoracic fluid condition. The initial assessment of thoracic impedance at blocks 202 and 204 may be performed on a periodic basis for making an initial non-specific detection of a thoracic fluid condition. Blocks 202 and 204 are optional precursors to performing the intrathoracic impedance measurement and computation and comparison methods for detecting and discriminating thoracic fluid conditions. Method 200 may be performed periodically beginning immediately with the sequential impedance measurements at block 206.

At block 206, sequential impedance measurements are performed. An initial excitation signal electrode pair is selected, and impedance measurements between remaining electrode pairs are made. The selected excitation electrode pair is used for injecting a current signal along an excitation path. The voltage is then measured across the remaining, sequentially selected, measuring electrode pairs allowing the impedance across each measurement vector to be computed from the known excitation signal and the measured voltage.

After each impedance measurement vector is selected, a new excitation signal electrode pair is selected and remaining electrodes are selected in measurement pairs. As discussed previously, measurements may be controlled to occur at times relative to other device sensing and therapy delivery operations. In some embodiments, impedance measurements may be controlled to occur at a selected time point in the cardiac cycle and/or in the respiratory cycle. The thoracic impedance will change cyclically with heart filling and emptying and with lung filling and emptying. As such, impedance measurements may be timed relative to cardiac and respiration cycles to reduce the effect of these normal cyclical variations.

It is further contemplated that impedance measurements may be acquired at particular times of day, at particular heart rates, activity levels, body posture. For example, impedance measurements may be acquired during nighttime hours and during daytime hours to obtain diurnal variations in impedance measurements. Increasing diurnal variation may be indicative of a more serious thoracic fluid condition.

At block 208, a conductivity map is computed from the internally measured impedances using impedance mapping methods such as finite element, finite different, and boundary element methods or other mathematical methods adapted from EIT or other impedance mapping techniques. Reference is made, for example, to the following articles, each of which is incorporated herein by reference: Wolf G K, et al., "Non-invasive assessment of lung volume: Respiratory inductance plethysmography and electrical impedance tomography", *Crit Care Med* 2005; 33(3) S163-S169, Bayford R H, "Bioimpedance tomography", *Annu Rev Biomed Eng.* 2006; 8:63-91, Coulombe N et al., "A parametric model of the relationship between EIT and total lung volume", *Physiol Meas* 2005; 26 (4):401-411, Zhang J, et al., "EIT images of ventilation: What contributes to the resistivity changes?" *Physiol Meas* 2005;26(2):S81-92.

The conductivity map is a data set relating each pixel to a computed conductivity. A conductivity map may be computed using the acquired measurements without applying initial conditions. Alternatively, anatomic or pixel boundary conditions and initial assumptions of tissue conductivity may be applied.

At block 210, the conductivity map data is stored in memory. The data may be retrieved and transmitted to an external device for further analysis or for generating a display of the conductivity map data at block 214. The display may not have adequate resolution for actually mapping anatomic structures but may be useful for highlighting localized pixels exhibiting a change in computed conductivity to aid the clinician in diagnosing and treating a thoracic fluid condition.

At block 212, the map data is compared to previously computed map data for localizing conductivity changes. The map data may be acquired on a periodic basis, such as daily or weekly so that previously stored data is available for comparison. The newly acquired map data is compared to previously acquired data to detect a change in conductivity representative of a change in extra-cellular fluid in the thorax. The newly acquired map data may be compared to a previous map, a running average of map data or a cumulative summation method may be implemented for detecting a change in conductivity. In the cumulative summation approach, the difference of each computed conductivity and a baseline conductivity for a pixel is computed and summed with previously determined differences. The cumulative sum determined for each pixel may then be compared to a predetermined threshold for detecting a clinically relevant change in conductivity.

If no pixels exhibit a change in conductivity sufficient to detect a thoracic fluid condition, method 200 returns to block 202. If any of the pixels exhibit a change in conductivity, a discrimination algorithm is performed at block 214. The discrimination algorithm involves applying a set of detection rules or criteria for detecting and discriminating a thoracic fluid condition based on localized conductivity changes. For each pixel exhibiting a change in conductivity, one or more detection rules may be applied. Details regarding the discrimination rules applied at block 214 are discussed below in conjunction with FIG. 7. Briefly, discrimination criteria corresponding to an anatomical region identified as having a change in conductivity in one or more pixel defining the anatomical region will be applied to those pixels. If the discrimination criteria are met, a notification is generated at block 216 to alert the patient and/or clinician or other caregiver of the detected thoracic fluid condition.

It is further contemplated that the multiple impedance measurements themselves may be used in identifying anatomic regions undergoing changes in impedance for use in detecting and discriminating thoracic fluid conditions. The multiple impedance measurement changes may be used alternatively to or in addition to mapped conductivity data. In one embodiment, impedance measurements are initially used to detect a thoracic fluid condition, and the conductivity map data is used to discriminate the type of condition present if the condition cannot be identified from the impedance data alone.

Figure 7:
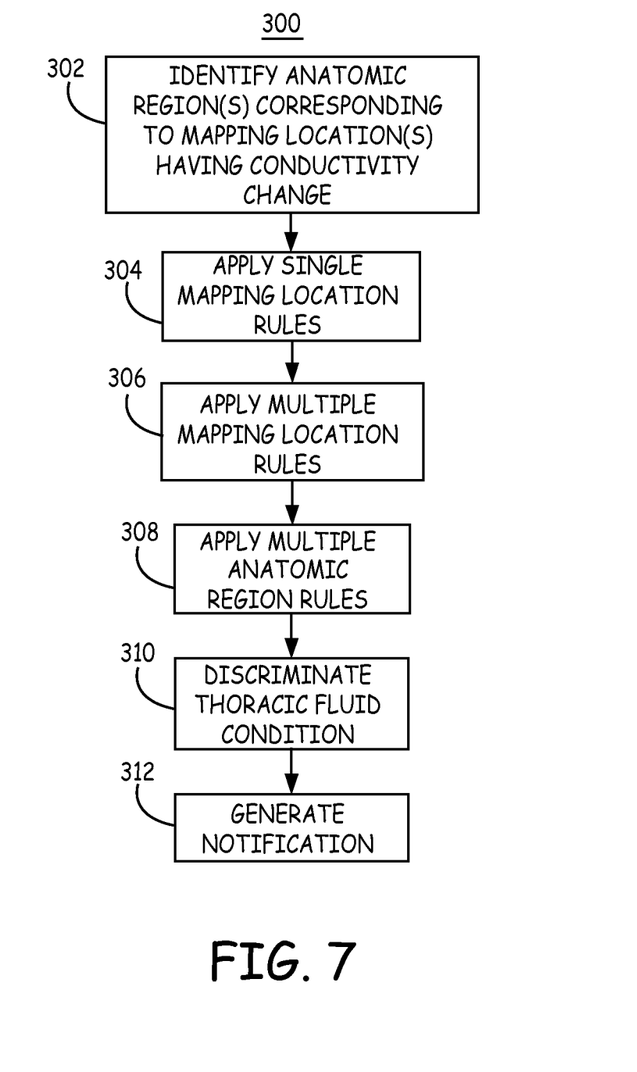
FIG. 7 is a flow chart of a method for discriminating thoracic fluid conditions based on a detected change in thoracic conductivity.

FIG. 7 is a flow chart of a method 300 for discriminating thoracic fluid conditions based on a detected change in conductivity. At block 302, an anatomic region is identified in which a conductivity change has been detected. A conductivity change may be detected in one or more mapping locations or pixels. As such, more than one anatomic region may be identified at block 302 as being a region including a pixel in which a conductivity change has been detected. Furthermore, one pixel may be included in more than one anatomic region. Particularly when the resolution of the conductivity map is low, globally or regionally, a single pixel may overlap two or more anatomic regions. In a generic example, an anatomic region A may be approximated by pixels 1, 2 and 3, and an anatomic region B may be approximated by pixels 3 and 4. As such, a change in a single pixel, pixel 3 in the foregoing example, may result in more than one anatomic region being identified at block 302. Furthermore, conductivity changes in multiple pixels may result in one or more anatomic regions being identified at block 302.

At blocks 304 through 308, a number of rules for discriminating the thoracic fluid condition are applied. Multiple rules may be applied to each anatomic region. For example, at block 304, single location rules may be applied which compare the detected conductivity change for a single pixel to a discrimination threshold. A discrimination threshold applied in any of blocks 304 through 308 may define both the amount of change in conductivity as well as the time duration of the change. If the change in conductivity in a single pixel exceeds a discrimination threshold, a thoracic fluid condition corresponding to the identified anatomic region may be detected. The threshold for discriminating a thoracic fluid condition based on a conductivity change at a single location may be greater than a threshold for initially detecting a change in conductivity at block 208 in FIG. 6. Conditions corresponding to edema or increased extracellular fluid will be detected based on increasing conductivity, e.g., a positive change in conductivity exceeding a discrimination threshold. It is recognized that thoracic fluid conditions that are detected and discriminated using method 300 can also include conditions corresponding to decreased extracelluar fluid, for example lung dryness that may occur when a patient is over-diuresed. As such, while illustrative embodiments described herein may refer to a conductivity change exceeding a threshold, that change may be a negative conductivity change corresponding to decreasing conductivity.

If a single location conductivity change exceeding a discrimination threshold corresponds to more than one anatomic region, additional rules may be applied before making a conclusion. If no other rules are satisfied, a generic notification may be generated at block 312 indicating an indiscriminate or non-specific thoracic fluid condition has been detected. The notification may include information indicating the corresponding anatomic regions and the conductivity trend. The conductivity trend may be expressed generally as an increasing wetness or increasing fluid trend or as an increasing dryness or decreasing fluid trend.

At block 306, rules or criteria relating to multiple mapping locations or pixels may be applied. In order to detect a thoracic fluid condition for a particular anatomic region, discrimination criteria may require that a minimum number of the total number of pixels approximating the anatomic region exhibit a conductivity change. Alternatively, staged discrimination criteria may be applied. Staged criteria would apply different conductivity change thresholds to different pixels and/or different change thresholds to different numbers of pixels within the anatomic region. By way of illustration, one pixel included in an approximated lung region may include bone or other tissue not expected to undergo significant conductivity changes. A second pixel included in the same approximated lung region might include substantially only lung tissue. In this case, a higher conductivity change threshold may be applied to the second region than the first region for discriminating pulmonary edema.

In another example of staged criteria, a single anatomic region may include several pixels, for example four pixels. If all four pixels exceed a low-level change threshold, a thoracic fluid condition for that anatomic region may be detected. If one of the pixels does not exceed the low-level threshold, but two to three pixels exceed a higher threshold the thoracic fluid condition may still be detected. If at least two of the pixels do not exceed the higher threshold, but any one pixel exceeds a still higher threshold, the thoracic fluid condition for that anatomic region may still be detected.

At block 308, rules are applied to multiple anatomic regions. Discrimination criteria may be applied for detecting a thoracic fluid condition that encompasses more than one anatomic region or to eliminate localized thoracic fluid condition detections when global or widespread conductivity changes are present. For example, a pulmonary edema condition may be discriminated between the left lung, the right lung or both lungs and further between posterior and anterior regions of each lung. A highly localized pulmonary edema may correspond to pneumonia whereas a more global pulmonary edema may correspond to pulmonary congestion due to heart failure. If increased conductivity is identified in a cardiac ventricle region in addition to a global pulmonary edema, cardiac dilation may also be occurring indicating a severe heart failure decompensation. As such, after applying single and multiple pixel rules at blocks 304 and 306, preliminary thoracic fluid conditions may be detected based on the anatomic regions affected. Additional rules may then be applied at block 308 to further discriminate the thoracic fluid condition(s) based on the anatomical, physiological and/or pathological relationships between the affected anatomic regions. Such relationships may contribute to the overall changes in thoracic fluid and therefore be pertinent in the specificity of the discrimination method 300.

Accordingly, discrimination methods applied at 308 may include grouping multiple affected anatomic regions into a common thoracic fluid condition detection or verifying that related anatomic regions do not exhibit an increased conductivity when detecting a localized or isolated thoracic fluid condition. In other words, in order to discriminate a localized thoracic fluid condition, rules applied at block 308 may require that neighboring pixels in neighboring anatomic regions do not exhibit a change in conductivity. If an anatomic region includes pixels that individually or collectively do not meet thoracic fluid condition detection criteria for that anatomic region but do exhibit a change in conductivity, that change may also be taken into consideration in making a discriminatory detection of a thoracic fluid condition in a related anatomic region.

At block 312, a notification is generated. The notification may be issued in the form of an IMD alarm perceivable by the patient, a data transfer to an external device from the IMD, a data transfer to a centralized database or computer, or an email message transmission or other data communication to a communication device. The notification may be directed to the patient or a clinician or other caregiver. The notification may include specific information regarding the discriminated thoracic fluid condition, the thoracic fluid trend, and may include specific actions to be taken by the patient for administering medication under a physician's supervision, seeking medical attention, or the like.

Method 300 for discriminating between thoracic fluid conditions, using a computed conductivity map, may be implemented using neural networks, heuristic, or statistical models such as multi-variate regression, or other methods including learning algorithms or belief networks such as a Baysian network.

The methods and associated apparatus described herein provide the potential for improved sensitivity and specificity in detecting thoracic fluid conditions. Specific thoracic fluid conditions may be detected based on both the time duration and the pixels of detected conductivity changes with detection and discrimination criteria uniquely defined for different conditions. As such, early and appropriate medical intervention may be enabled.

Thus, methods and associated apparatus for detecting and discriminating thoracic fluid conditions have been presented in the foregoing description with reference to specific embodiments. It is appreciated that various modifications to the referenced embodiments may be made without departing from the scope of the invention as set forth in the following claims.

The invention claimed is:

1. A method of detecting a thoracic fluid condition in an implantable medical device system, comprising:
periodically measuring intrathoracic impedance for one of a plurality of intrathoracic measurement vectors using a pair of a plurality of electrodes implanted along the thoracic cavity of a patient, the one of the plurality of intrathoracic measurement vectors selected as representative of a global intrathoracic impedance of the patient, wherein the global intrathoracic impedance is sensitive to an intrathoracic impedance change with low specificity as to a location of the intrathoracic impedance change;
detecting, based on the periodic measurements, the intrathoracic impedance change for the one of the plurality of intrathoracic measurement vectors representative of the global intrathoracic impedance of the patient, wherein the intrathoracic impedance change is a trigger for intrathoracic impedance measurements for the plurality of intrathoracic measurement vectors;
in response to detecting the intrathoracic impedance change, measuring intrathoracic impedance for the plurality of intrathoracic measurement vectors using the plurality of electrodes;
in response to measuring the intrathoracic impedances, computing a conductivity of each of a plurality of intrathoracic impedance mapping locations corresponding to the plurality of intrathoracic measurement vectors, wherein each of a plurality of anatomic regions is associated with a respective one or more of the mapping locations;
detecting a change in conductivity for one or more of the mapping locations based on the computed conductivities of the mapping locations;
detecting the thoracic fluid condition in response to the detected change in conductivity; and
discriminating, by a processor, within which one or more of the plurality of anatomic regions the thoracic fluid condition occurred based upon for which of the mapping locations the change in conductivity was detected.

2. The method of claim 1 wherein detecting the change in the computed conductivity comprises:
determining a baseline conductivity for each of the plurality of mapping locations;
computing a cumulative sum of differences between the computed conductivity and the baseline conductivity over time for each of the plurality of mapping locations; and
comparing each of the cumulative sums to a conductivity change threshold.

3. The method of claim 1 wherein discriminating the detected thoracic fluid condition comprises applying detection criteria to a group of the mapping locations which collectively define a first anatomic region of the plurality of anatomic regions.

4. The method of claim 3 wherein discriminating the detected thoracic fluid condition further comprises:
applying detection criteria to a second group of the mapping locations which collectively define a second anatomic region of the plurality of anatomic regions different than the first anatomic region; and
detecting a global thoracic condition when both the first and the second anatomic regions are affected.

5. The method of claim 1 wherein discriminating within which one or more of the plurality of anatomic regions the thoracic fluid condition occurred comprises discriminating within which one or more of a heart region, a lung region, and an implantable medical device pocket region the thoracic fluid condition occurred based upon for which of the mapping locations the change in conductivity was detected.

6. The method of claim 1 wherein discriminating within which one or more of the plurality of anatomic regions the thoracic fluid condition occurred comprises discriminating within which one or more of a left posterior region, a right posterior region, a left anterior region, and a right anterior region the thoracic fluid condition occurred based upon for which of the mapping locations the change in conductivity was detected.

7. An implantable medical device, comprising;
a plurality of electrodes configured to be implanted along the thoracic cavity of a patient;
an impedance measuring module configured to periodically measure intrathoracic impedance for one of a plurality of intrathoracic measurement vectors using a pair of the plurality of electrodes implanted along the thoracic cavity of the patient, the one of the plurality of intrathoracic measurement vectors selected as representative of a global intrathoracic impedance of the patient, wherein the global intrathoracic impedance is sensitive to an intrathoracic impedance change with low specificity as to a location of the intrathoracic impedance change;
a processor configured to detect, based on the periodic measurements, the intrathoracic impedance change for the one of the plurality of intrathoracic measurement vectors representative of the global intrathoracic impedance of the patient, wherein the intrathoracic impedance change is a trigger for intrathoracic impedance measurements for the plurality of intrathoracic measurement vectors, and wherein the impedance measuring module is configured to, in response to the detection of the intrathoracic impedance change, measure intrathoracic impedance for the plurality of intrathoracic measurement vectors between the plurality of electrodes; and
a mapping module configured to, in response to the intrathoracic impedances being measured, compute a conductivity of each of a plurality of intrathoracic impedance mapping locations corresponding to the plurality of intrathoracic impedance measurement vectors, wherein each of a plurality of anatomic regions is associated with a respective one or more of the mapping locations, wherein
the processor is configured to detect a change in conductivity for one or more of the mapping locations based on the computed conductivities of the mapping locations, detect a thoracic fluid condition in response to the change in conductivity being detected, and discriminate within which one or more of the plurality of anatomic regions the thoracic fluid condition occurred based upon for which of the mapping locations the change in conductivity was detected.

8. The device of claim 7 wherein the processor is configured to, for detection of the change in the computed conductivity, determine a baseline conductivity for each of the plurality of mapping locations, compute a cumulative sum of differences between the computed conductivity and the baseline conductivity over time for each of the plurality of mapping locations, and compare each of the cumulative sums to a conductivity change threshold.

9. The device of claim 7 wherein the processor is configured to apply detection criteria to a group of the mapping locations which collectively define a first anatomic region of the plurality of anatomic regions to discriminate the detected thoracic fluid condition.

10. The device of claim 9 wherein, for discriminating the detected thoracic fluid condition, the processor is configured to:
apply detection criteria to a second group of the mapping locations which collectively define a second anatomic region of the plurality of anatomic regions different than the first anatomic region; and
detect a global thoracic condition when both the first and the second anatomic regions are affected.

11. The device of claim 7 wherein the processor is configured to discriminate within which one or more of a heart region, a lung region, and an implantable medical device pocket region the thoracic fluid condition occurred based upon for which of the mapping locations the change in conductivity was detected.

12. The device of claim 7 wherein the processor is configured to discriminate within which one or more of a left posterior region, a right posterior region, a left anterior region, and a right anterior region the thoracic fluid condition occurred based upon for which of the mapping locations the change in conductivity was detected.

13. A system for detecting a thoracic fluid condition in an implantable medical device, comprising:
means for periodically measuring intrathoracic impedance for one of a plurality of intrathoracic measurement vectors using a pair of a plurality of electrodes implanted along the thoracic cavity of a patient, the one of the plurality of intrathoracic measurement vectors selected as representative of a global intrathoracic impedance of the patient, wherein the global intrathoracic impedance is sensitive to an intrathoracic impedance change with low specificity as to a location of the intrathoracic impedance change;
means for detecting, based on the periodic measurements, the intrathoracic impedance change for the one of the plurality of intrathoracic measurement vectors representative of the global intrathoracic impedance of the patient, wherein the intrathoracic impedance change is a trigger for intrathoracic impedance measurements for the plurality of intrathoracic measurement vectors;
means for, in response to detecting the intrathoracic impedance change, measuring intrathoracic impedance for the plurality of intrathoracic measurement vectors;
means for, in response to measuring the intrathoracic impedances, computing a conductivity of each of a plurality of intrathoracic impedance mapping locations corresponding to the plurality of intrathoracic measurement vectors, wherein each of a plurality of anatomic regions is associated with a respective one or more of the mapping locations;
means for detecting a change in conductivity for one or more of the mapping locations based on the computed conductivities of the mapping locations;
means for detecting the thoracic fluid condition in response to the detected change in conductivity; and
means for discriminating within which one or more of the plurality of anatomic regions the thoracic fluid condition occurred based upon for which of the mapping locations the change in conductivity was detected.

14. The method of claim 1, further comprising creating a plurality of isopotential lines with an excitation current from an electrode pair, wherein each of the intrathoracic impedance mapping locations correspond to a respective intersection between the isopotential lines and measurement vectors.

15. The method of claim 14, wherein the intrathoracic impedance mapping locations create a two dimensional grid of computed conductivities within the thoracic cavity of the patient.

16. The method of claim 1, wherein the thoracic fluid condition comprises pulmonary edema.

17. The method of claim 1, wherein the thoracic fluid condition comprises cardiac dilation.

18. The method of claim 1, wherein the thoracic fluid condition comprises acute anemia.

19. The method of claim 1, wherein the thoracic fluid condition comprises an implanted device pocket infection.

20. The method of claim 1, wherein the plurality of electrodes are carried by at least one of a subcutaneously implanted medical device or one or more subcutaneously implanted leads coupled to the implanted medical device, the subcutaneously implanted medical device and the one or more subcutaneously implanted leads being implanted outside of a ribcage of the patient.

* * * * *